United States Patent [19]

Yamaguchi

[11] Patent Number: 5,107,838
[45] Date of Patent: Apr. 28, 1992

[54] METHOD OF LEFT VENTRICULAR VOLUME EVALUATION USING NUCLEAR MAGNETIC RESONANCE IMAGING

[75] Inventor: Kojiro Yamaguchi, Tokyo, Japan

[73] Assignee: Kabushiki Kaisha Toshiba, Kanagawa, Japan

[21] Appl. No.: 652,120

[22] Filed: Feb. 7, 1991

[30] Foreign Application Priority Data

Feb. 8, 1990 [JP] Japan .................. 2-29207

[51] Int. Cl.$^5$ .................. A61B 5/055
[52] U.S. Cl. .................. 128/653.2; 128/713
[58] Field of Search .......... 128/713, 653 A, 661.04, 128/660.07

[56] References Cited

U.S. PATENT DOCUMENTS

| | | | |
|---|---|---|---|
| 4,197,836 | 4/1980 | Wagner et al. | 128/713 |
| 4,326,539 | 4/1982 | Obermajer | 128/713 |
| 4,674,518 | 6/1987 | Salo | 128/713 |
| 4,716,904 | 1/1988 | Meno | 128/654 |

*Primary Examiner*—Ruth S. Smith
*Attorney, Agent, or Firm*—Limbach & Limbach

[57] ABSTRACT

A method of left ventricular volume evaluation capable of obtaining an accurate evaluation of the left ventricular volume for a heart in an unaffected state. In the method, right anterior oblique image and 4-chamber image of the heart are obtained; using a nuclear magnetic resonance imaging, contours of the left ventricle in the right anterior oblique image and the 4-chamber image are determined; prescribed sets of sizes for the left ventricle are measured from the determined contours; and the volume of the left ventricle is evaluated by using an orthogonal biplane Simpson's method and the measured sizes.

6 Claims, 9 Drawing Sheets

METHOD OF LEFT VENTRICULAR VOLUME EVALUATION USING NUCLEAR MAGNETIC RESONANCE IMAGING

BACKGROUND OF THE INVENTION

1. Field of the Invention

The present invention relates to a method of left ventricular volume evaluation, and more particularly, to a method of left ventricular volume evaluation in which nuclear magnetic resonance imaging is utilized.

2. Description of the Background Art

In the diagnosis of the heart, it is clinically important to know the left ventricular volume accurately, because of the importance of the function of the left ventricle in the heart. As examples of a conventional method for evaluating this left ventricular volume, several methods including an intracardiac catheterization method, a radiocardiography (cardiac radioactive isotope) method, and an echocardiography method are known.

In the intracardiac catherization method, a contrast medium is injected into the heart, and the contour of the left ventricle is X-ray imaged by utilizing the contrast produced by the irradiation of X-ray, such that the left ventricular volume can be evaluated on a basis of the X-ray imaged left ventricular contour. Now, in such an intracardiac catheterization, the X-ray image of the left ventricle is a projection from a point X-ray source, so that the X-ray imaged left ventricular contour is enlarged compared with the actual size, and there is a need to take the enlarging rate into account in order to evaluate the left ventricular volume accurately. However, the determination of this enlarging rate requires the accurate knowledge of the distances among the X-ray source, left ventricle, and X-ray film, so that the accurate determination of the enlarging rate has been impossible, and consequently the accurate evaluation of the left ventricular volume using the intracardiac catheterization has been impossible.

Moreover, in the intracardiac catheterization method, the injection of the contrast medium affects the state of the heart and causes a change of the size of the left ventricle from its normal size, so that the accurate evaluation of the left ventricular volume is actually impossible.

In the radiocardiography method, the radioactive isotope is used instead of the contrast medium in the intracardiac catheterization method, and the X-ray image of the left ventricular contour is obtained and utilized in a manner similar to the intracardiac catheterization method. In this radiocardiography method, the sensitivity of the radioactive isotope detector is rather low, so that the accurate imaging of the left ventricular contour is impossible, and consequently the accurate evaluation of the left ventricular volume using the radiocardiography has been impossible.

In the echocardiography method, the left ventricular contour is obtained by using the echos resulting from the irradiation of ultrasonic waves by an ultrasonography apparatus, and the left ventricular volume is evaluated on a basis of the obtained left ventricular contour. However, in such an echocardiography, the radiation angle for the ultrasonic waves emitted from the ultrasonic probe is small, i.e., a region of irradiation by the ultrasonic waves is small, so that there have been situations in which it is impossible to take an entire image of the heart, and consequently the accurate evaluation of the left ventricular volume using the echocardiography has been impossible.

SUMMARY OF THE INVENTION

It is therefore an object of the present invention to provide a method of left ventricular volume evaluation capable of obtaining an accurate evaluation of the left ventricular volume for a heart in an unaffected state, by utilizing nuclear magnetic resonance imaging.

This object is achieved in the present invention by providing a method of evaluating a volume of a left ventricle of a heart, comprising the steps of: obtaining a right anterior oblique image and a 4-chamber image of the heart using nuclear magnetic resonance imaging, where the right anterior oblique image and the 4-chamber image are tomographic images for planes intersecting perpendicularly with each other at a straight line joining a mitral valve and a left ventricle apex; determining contours of the left ventricle in the right anterior oblique image and the 4-chamber image obtained at the obtaining step; measuring prescribed sets of sizes for the left ventricle from the contours determined at the determining step; and evaluating the volume of the left ventricle by using an orthogonal biplane Simpson's method and the sizes measured at the measuring step.

Other features and advantages of the present invention will become apparent from the following description taken in conjunction with the accompanying drawings.

DETAILED DESCRIPTION OF THE PREFERRED EMBODIMENTS

Now, one embodiment of a method of left ventricular volume evaluation according to the present invention will be described in detail.

First, referring to FIG. 1, a nuclear magnetic resonance imaging apparatus to be utilized in the present invention will be described.

Figure 1:
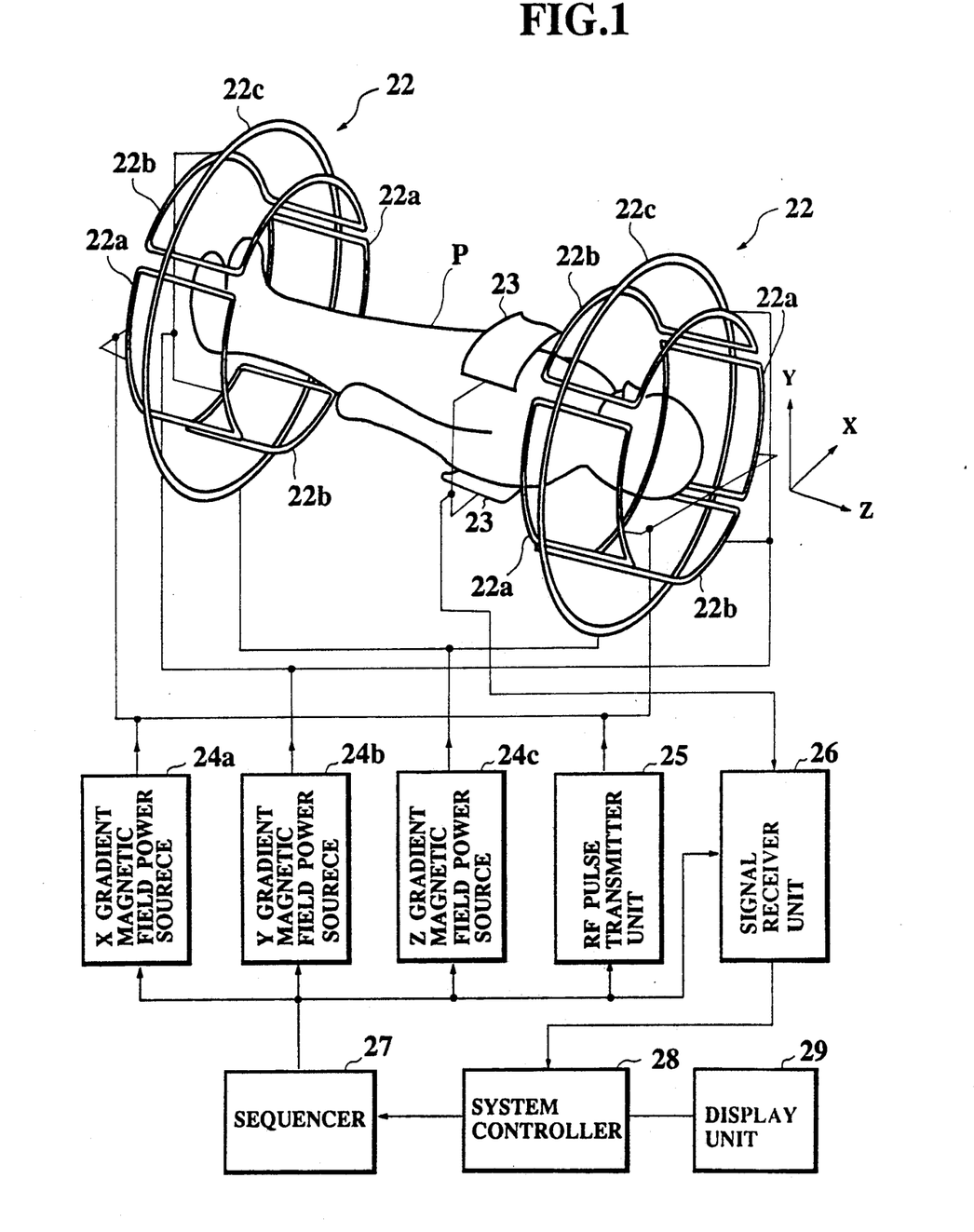
FIG. 1 is a schematic block diagram of a nuclear magnetic resonance imaging apparatus to be utilized in an embodiment of a method of left ventricular volume evaluation according to the present invention.

This apparatus of FIG. 1 comprises: a main magnet (not shown) for generating a static magnetic field around a patient P; gradient magnetic field coils 22 for generating gradient magnetic fields to be superposed onto the static magnetic fields; and an RF probe coil 23 for generating the RF pulses to be applied to the patient P and detecting the nuclear magnetic resonance echo signals from the patient P.

The gradient magnetic field coils 22 include: a set of X gradient magnetic field coils 22a connected to an X gradient magnetic field power source 24a for generating the gradient magnetic field in an X direction; a set of Y gradient magnetic field coils 22b connected to a Y gradient magnetic field power source 24b for generating the gradient magnetic field in a Y direction; and a set of Z gradient magnetic field coils 22c connected to a Z gradient magnetic field power source 24c for generating the gradient magnetic field in a Z direction; where X, Y and Z directions are defined as shown in FIG. 1.

The RF probe coil 23 is connected to an RF pulse transmitter unit 25 for providing the RF pulses to the RF probe coil 23, and a signal receiver unit 26 for receiving the nuclear magnetic resonance echo signals detected by the RF probe coil 23.

The apparatus of FIG. 1 further comprises: a sequencer 27 for controlling pulse sequences to be executed by the gradient magnetic field coils 22 and the RF probe coil 23; a system controller 28 for controlling operations of the elements of the apparatus, and processing the received nuclear magnetic resonance echo signals; and a display unit 29 for displaying nuclear magnetic resonance images obtained by processing the nuclear magnetic resonance echo signals.

Now, the procedure of this embodiment of a method of left ventricular volume evaluation using the above described apparatus will be described in detail.

In this method, positioning for the sake of taking a 4-chamber image and a RAO (right anterior oblique) image is performed according to the following steps (A)-(H).

Figure 2:
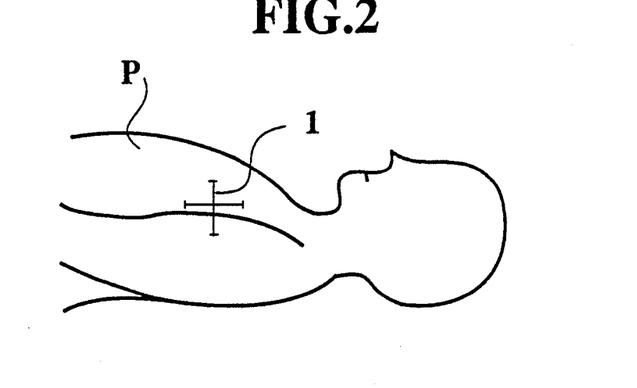
FIG. 2 is a side view of a patient for explaining a positioning of an imaging target.

(A) First, as shown in FIG. 2, the positioning of an imaging target on the patient P is performed by using a projector. Namely, as shown by a cross shaped projection 1, the imaging target is set to approximately one third of the thickness of the patient's body from a front side of the patient P. Then, an ECG electrode is attached to the patient P so that the information on an electrocardiogram and other information which is needed in determining the imaging conditions are obtained by using a heart beat and respiration synchronizer unit and an electrocardiogram monitor.

Then, the pilot scan in the coronal plane is carried out under the imaging condition settings summarized in the following Table 1.

TABLE 1

| IM | TR (msec) | TE (msec) | TI (msec) | FA (deg) | NS | NE | NA (times) | ST (mm) | GT | MX |
|----|-----------|-----------|-----------|----------|-----|-----|------------|---------|-----|-----|
| FE | 50 | 22 | 0 | 30 | 5 | 1 | 4 | 15 | NL | QS |

In Table 1, IM stands for the imaging method, FE stands for the field echo method, TR stands for the repetition time, TE stands for the echo time, TI stands for the inversion recovery time, FA stands for the flip angle, NS stands for the number of slices, NE stands for the number of echos, NA stands for the number of averagings, ST stands for the slice thickness, GT stands for the gate mode, NL stands for null, MX stands for the matrix, and QS stands for the quick scan.

Figure 3:
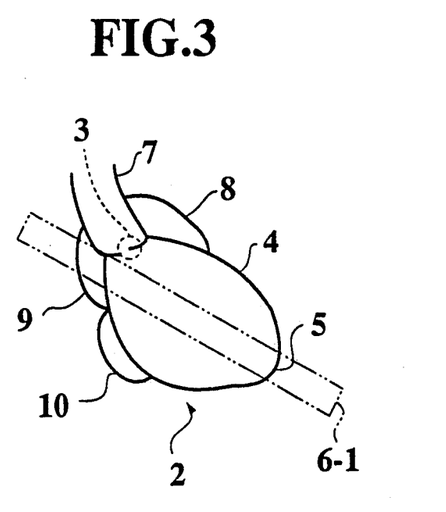
FIGS. 3 to 8 are illustrations of intermediate tomographic images obtained in a course of the method of left ventricular volume evaluation according to the present invention.

As a result of this pilot scan, the coronal tomographic image of the heart 2 along the body axis shown in FIG. 3 can be obtained.

(B) Next, as shown in FIG. 3, on the coronal tomographic image of the heart 2 obtained at the step (A), an ROI (region of interest) 6-1 for positioning is formed along a straight line joining a lower side of an aortic valve 3 and a left ventricle apex 5. FIG. 3 also shows an aorta 7, a left atrium 8, a right atrium 9, and a right ventricle 10. After the ROI 6-1 is formed, the imaging along the ROI 6-1 is carried out under the imaging condition settings summarized in the following Table 2.

TABLE 2

| IM | TR (msec) | TE (msec) | TI (msec) | FA (deg) | NS | NE | NA (times) | ST (mm) | GT | MX |
|----|-----------|-----------|-----------|----------|-----|-----|------------|---------|-----|-----|
| FE | 50 | 22 | 0 | 30 | 1 | 1 | 4 | 10 | NL | QS |

Figure 4:
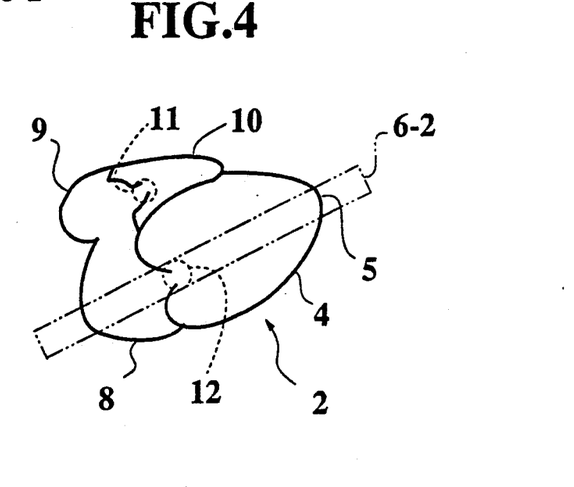

As a result of this imaging, the tomographic image of the heart 2 shown in FIG. 4 can be obtained.

(C) Next, as shown in FIG. 4, on the tomographic image of the heart 2 obtained at the step (B), another ROI 6-2 for positioning is formed along a straight line passing through a widest region in the left atrium 8. FIG. 4 also shows a tricuspid valve 11, and a mitral valve 12. After the ROI 6-2 is formed, the imaging along the ROI 6-2 is carried out under the same imaging condition settings summarized in the Table 2 above.

Figure 5:
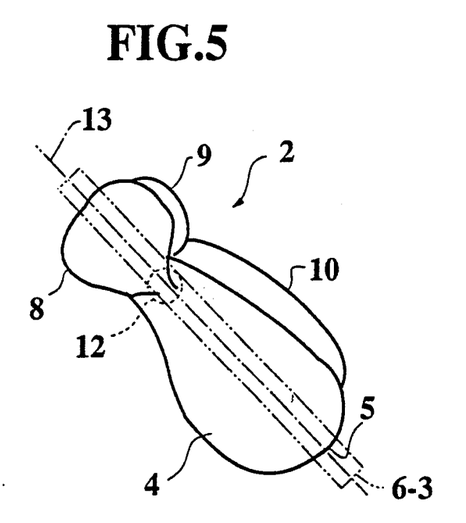

As a result of this imaging, the tomographic image of the heart 2 shown in FIG. 5 can be obtained.

(D) Next, as shown in FIG. 5, on the tomographic image of the heart 2 obtained at the step (C), another ROI 6-3 for positioning is formed along a straight line passing through the mitral valve 12 and the left ventricle apex 5, i.e., a straight line on an axis 13 of the heart 2. After the ROI 6-3 is formed, the imaging along the ROI 6-3 is carried out under the same imaging condition settings summarized in the Table 2 above.

Figure 6:
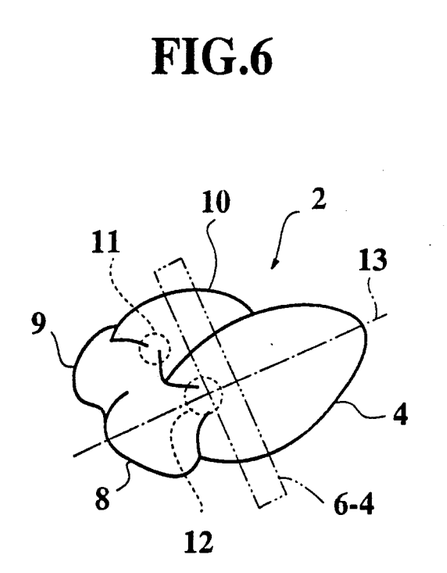

As a result of this imaging, the tomographic image of the heart 2 for a plane containing the axis 13 shown in FIG. 6 can be obtained.

(E) Next, as shown in FIG. 6, on the tomographic image of the heart 2 obtained at the step (D), another ROI 6-4 for positioning is formed along a straight line perpendicular to the axis 13 of the heart 2 at an edge of the mitral valve 12. After the ROI 6-4 is formed, the imaging along the ROI 6-4 is carried out under the same imaging condition settings summarized in the Table 2 above.

Figure 7:
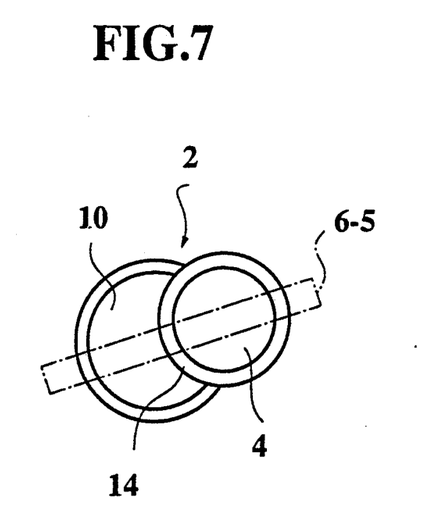

As a result of this imaging, the tomographic image of the heart 2 shown in FIG. 7 can be obtained.

(F) Next, as shown in FIG. 7, on the tomographic image of the heart 2 obtained at the step (E), another ROI 6-5 for positioning is formed along a straight line passing through the center of the left ventricle 4 and the center of the interventricular septum 14. After the ROI 6-5 is formed, the imaging along the ROI 6-5 is carried out under the same imaging condition settings summarized in the Table 2 above.

Figure 8:
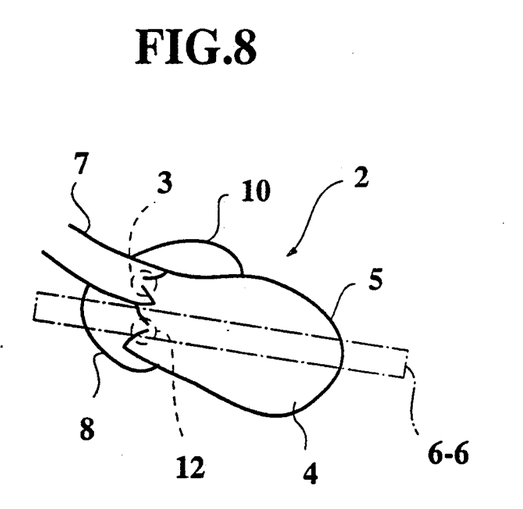

As a result of this imaging, the tomographic image of the heart 2 shown in FIG. 8 can be obtained.

(G) Next, as shown in FIG. 8, on the tomographic image of the heart 2 obtained at the step (F), another ROI 6-6 for positioning is formed along a straight line passing through the mitral valve 12 and the left ventricle apex 5. After the ROI 6-6 is formed, the imaging along the ROI 6-6 is carried out under the same imaging condition settings summarized in the Table 2 above.

Figure 9:
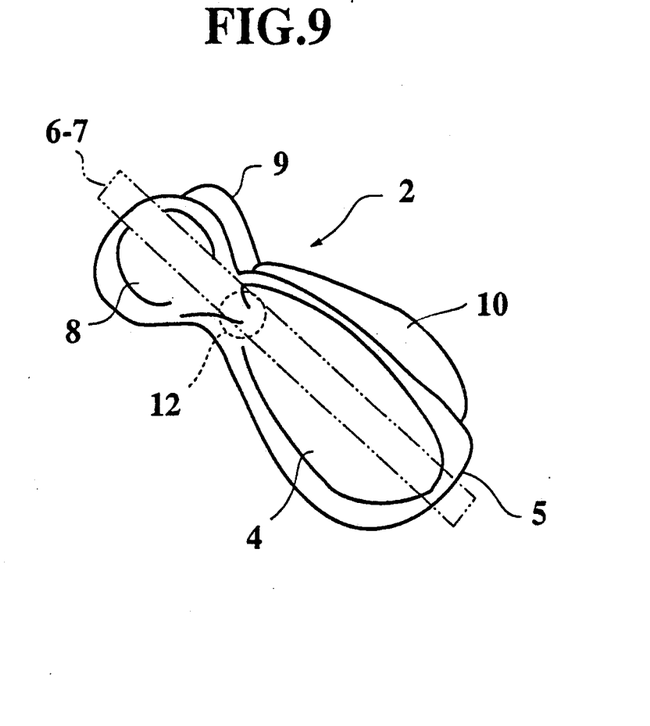
FIG. 9 is an illustration of a right anterior oblique image obtained in a course of the method of left ventricular volume evaluation according to the present invention.

As a result of this imaging, the tomographic image of the heart 2 shown in FIG. 9 can be obtained.

This tomographic image of FIG. 9 represents a true RAO (right anterior oblique) projection containing a straight line joining the left ventricle apex 5 and the mitral valve 12.

At this point, it is preferable to confirm the true RAO projection at a higher image quality obtained by synchronous imaging. To this end, the cine imaging of this RAO projection is achieved by positioning the projection of FIG. 8 at sample planes and by carrying out imaging under the same imaging condition setting summarized in the following Table 3.

TABLE 1

| IM | TR (msec) | TE (msec) | TI (msec) | FA (deg) | NS | NE | NA (times) | ST (mm) | GT | MX |
|---|---|---|---|---|---|---|---|---|---|---|
| FE | 800 | 22 | 0 | 30 | 1 | 1 | 8 | 10 | S | QS |

In Table 3, S stands for the single slice multi-phase, and the setting of TR corresponds to a condition for a case in which the interval between the R waves in the electro-cardiographic waves is 1000 msec.

(H) Furthermore, as shown in FIG. 9, on the RAO image of the heart 2 obtained at the step (G), another ROI 6-7 for positioning is formed along a straight line passing through the mitral valve 12 and the left ventricle apex 5. After the ROI 6-7 is formed, the imaging along the ROI 6-7 is carried out under the same imaging condition settings summarized in the Table 2 above.

Figure 10:
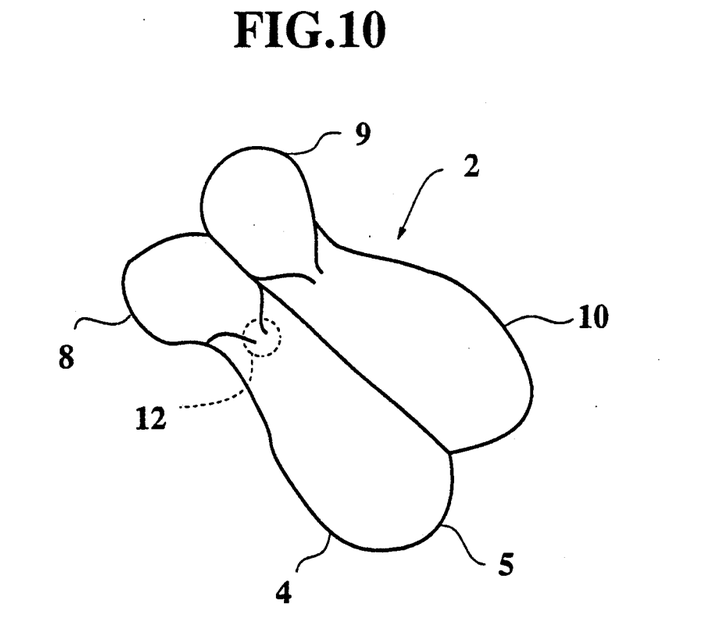
FIG. 10 is an illustration of a 4-chamber image obtained in a course of the method of left ventricular volume evaluation according to the present invention.

As a result of this imaging, the tomographic image of the heart 2 shown in FIG. 10 can be obtained.

This tomographic image of FIG. 10 is a 4-chamber image for a plane perpendicular to the RAO projection.

Now, on a basis of the position and image information from the RAO image and the 4-chamber image obtained by the positioning procedure described above, the left ventricular volume is evaluated by using the orthogonal biplane Simpson's method as follows.

Figure 11:
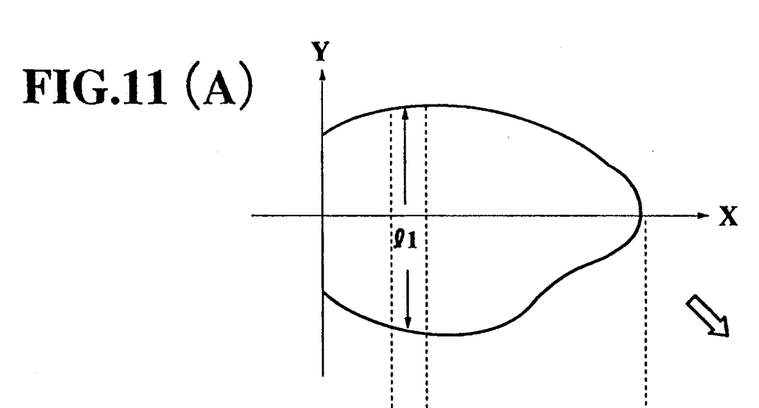
FIGS. 11(A) and 11(B) are illustrations of a contour obtained from the right anterior oblique image of FIG. 9, and a contour obtained from the 4-chamber image of FIG. 10, respectively.
FIG. 11(C) is an illustration of a three-dimensional model constructed by using the contours of FIGS. 11(A) and 11(B).

Namely, first a RAO projection contour shown in FIG. 11(A) and a 4-chamber projection contour shown in FIG. 11(B) are obtained from the RAO image of FIG. 9 and the 4-chamber image of FIG. 10. The procedure for obtaining these contours from the images will be described below.

Then, from the RAO projection contour of FIG. 11(A) and the 4-chamber projection contour of FIG. 11(B), diameters $l_1$ and $l_2$, respectively, at each cross section of width equal to L/n are obtained, where L is a long axis length of the left ventricle, and n is a number of divisions in a long axis direction. Then, assuming that the cross sectional shape of the left ventricle is an ellipse and each cross section of width equal to L/n corresponds to one pixel of the tomographic image, three-dimensional model shown in FIG. 11(C) is constructed by using $l_1$ and $l_2$ as the major and minor axes of an ellipse, respectively. Then, by using such a three-dimensional model for all the cross sections of width equal to L/n, the left ventricular volume V can be evaluated by the orthogonal biplane Simpson's method according to the following equation (1).

$$V(\text{ml}) = \sum_{\lambda=1}^{n} \{\pi \times (l_{1\lambda} \cdot l_{2\lambda}/4) \times (L/n)\} \quad (1)$$

where $\lambda$ is an index labelling each cross section of width equal to L/n.

In this manner, the accurate image of the left ventricle can be obtained by deriving the major and minor axes from the RAO projection and the 4-chamber projection. In addition, the orthogonal biplane Simpson's method can provide 99 to 100% accuracy in the left ventricular volume evaluation. Thus, according to this embodiment, it is possible to provide a method of left ventricular volume evaluation capable of obtaining an accurate evaluation of the left ventricular volume for a heart in an unaffected state.

Now, the procedure for obtaining the RAO projection contour of FIG. 11(A) and the 4-chamber projection contour of FIG. 11(B) from the RAO image of FIG. 9 and the 4-chamber image of FIG. 10 will be described in detail.

Figure 12:
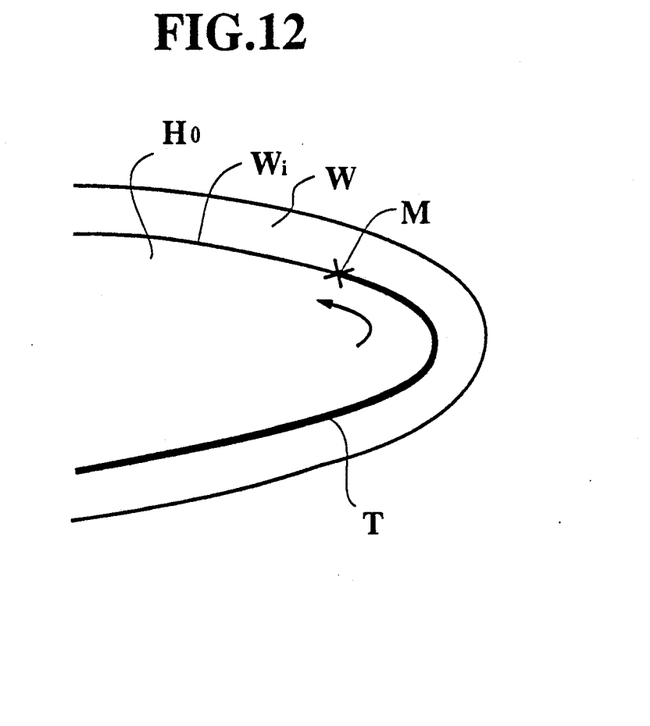
FIG. 12 is an illustration of a displayed tomographic image of a portion of a left ventricle for explaining one procedure for determining a contour from the tomographic image.

One possible procedure is a conventionally known one in which the contour is obtained on the displayed image by the manual operation of an operator as shown in FIG. 12. Namely, the operator traces an inner contour Wi of the cardiac muscle W with a cross shaped marker M whose position on the display is controlled by the manual operation of a mouse by the operator, so as to draw a boundary line T which forms the contour. This procedure utilizes the fact that a point in the cardiac muscle W appears on the display with higher density than a point in the cardiac cavity $H_0$ and a point in the region outside the cardiac muscle W. However, this procedure can be quite tedious for the operator, because this manual procedure may have to be performed on a great number of images.

Figure 13:
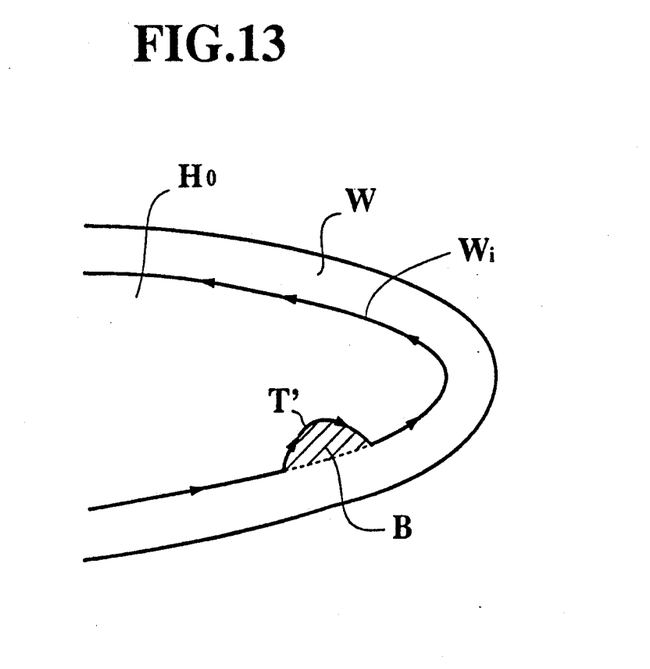
FIG. 13 is an illustration of a displayed tomographic image of a portion of a left ventricle for explaining a problem associated with the procedure explained in FIG. 12.

For this reason, there is an automatic boundary generation program which performs the above described boundary generation procedure automatically. However, the use of such an automatic boundary generation program has a problem in a case shown in FIG. 13 in which there is a high density blood tumor B inside the cardiac cavity $H_0$ near the cardiac muscle W. Namely, in such a case, the boundary may not be drawn along the inner contour Wi of the cardiac muscle W, and an erroneous boundary T' shown in FIG. 13 which goes around the blood tumor B may be obtained.

Figure 14:
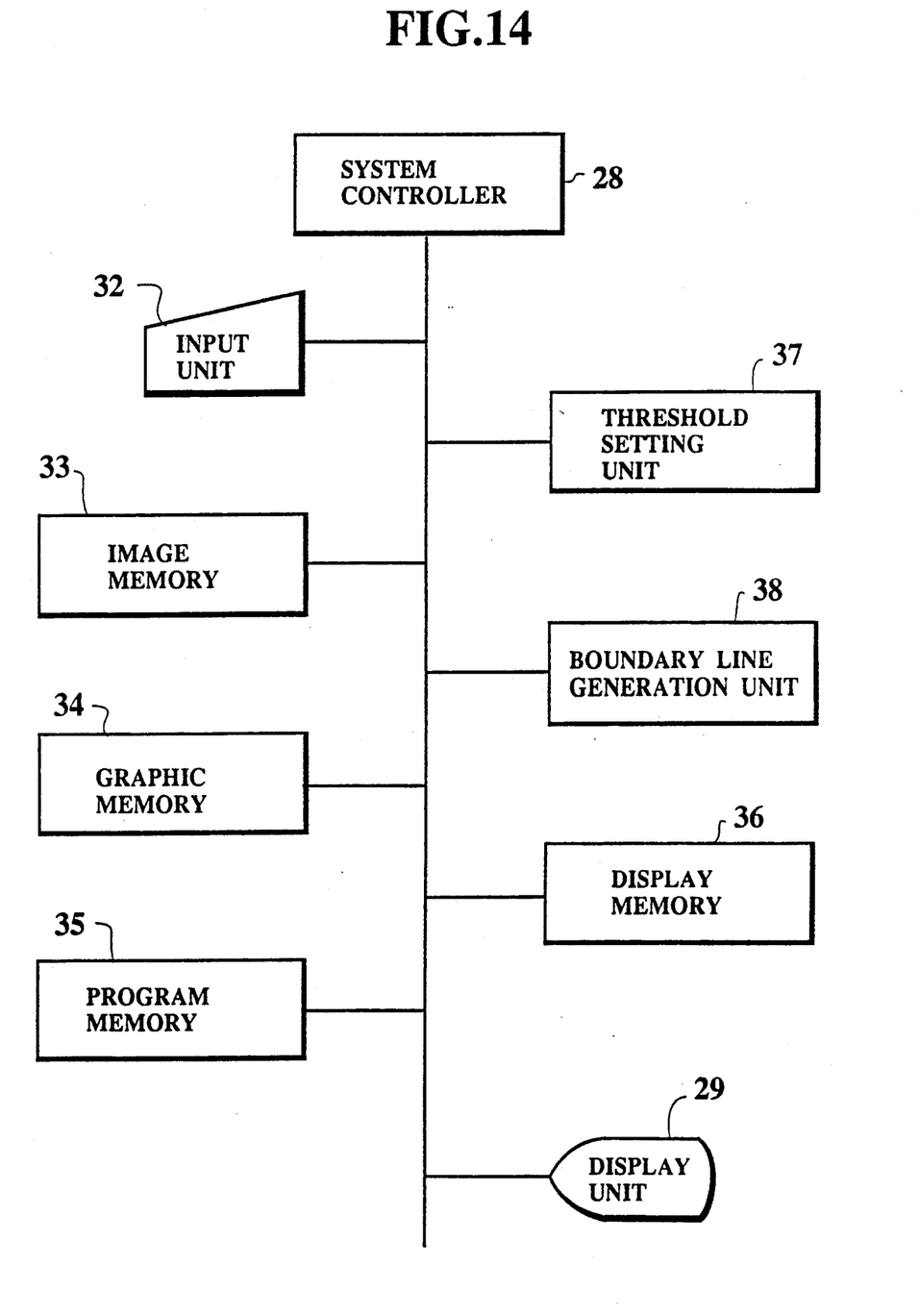
FIG. 14 is a schematic block diagram of a portion for extracting a contour from an image in a nuclear magnetic resonance imaging apparatus of FIG. 1.

This problem can be resolved by the following alternative procedure using an apparatus setting of FIG. 14.

In this setting of FIG. 14, the apparatus of FIG. 1 further comprises: an input unit 32 including a mouse for pointing to a coordinate on the display unit 29 and a keyboard for enabling a selection of a particular image of interest; an image memory 33 for storing data for the nuclear magnetic resonance images obtained by the apparatus; a graphic memory 34 for storing various graphic data such as a cross shaped marker M and radial lines L3 to be utilized in the procedure described below; a program memory 35 for memorizing a contour extraction program to be executed in the procedure described below; a display memory 36 for temporarily storing the image data of the image to be displayed on the display unit 29; a threshold setting unit 37 for setting appropriate upper and lower threshold values to be used in the procedure described below; and a boundary line generation unit 38 for extracting the contour by drawing the boundary line T through coordinates having a half value of the upper and lower threshold values set by the threshold setting unit 37, in accordance with the contour extraction program memorized by the program memory 35. The operation of these elements are also controlled by the system controller 28.

By using this setting, the procedure for obtaining the contour from the image proceeds as follows.

First, the operator selects the image data of interest by using the keyboard of the input unit 32. In response, the system controller 28 reads the selected image data from the image memory 33 and transmits the selected image data to the display memory 36 so as to have the image given by the selected image data displayed on the display unit 29.

Then, the system controller 28 reads the contour extraction program from the program memory 35 and executes this contour extraction program as follows.

Figure 15:
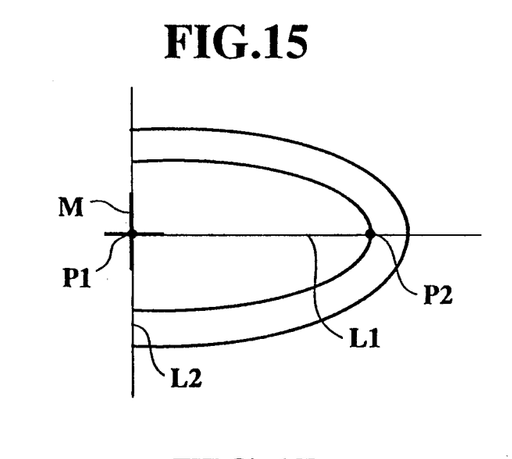
FIGS. 15 to 17 are illustrations of a displayed tomographic image of a portion of a left ventricle for explaining another procedure for determining a contour from the tomographic image.

Namely, as shown in FIG. 15, the operator first specifies the coordinates of the base P1 of the valve portion and the apex P2 of the cardiac cavity portion by pointing to them with the cross shaped marker M by operating the mouse of the input unit 32.

When these coordinates are specified, the boundary line generation unit 38 draws a long axis L1 joining the specified base P1 and apex P2 and a short axis L2 intersecting with the long axis L1 perpendicularly at the base P1 over the displayed image by using the line segment data stored in the graphic memory 34.

Figure 16:
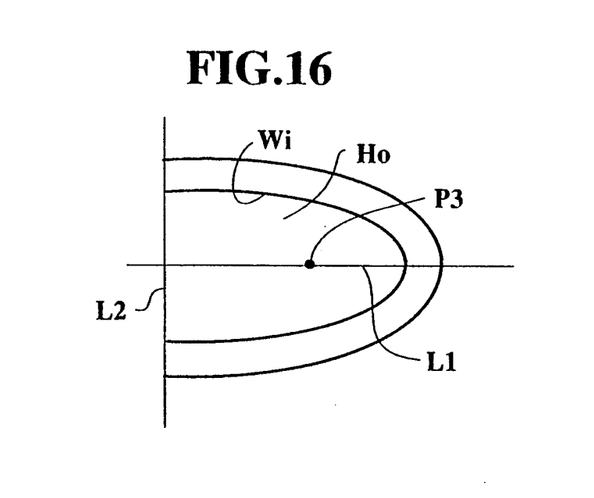

Next, as shown in FIG. 16, the operator specifies the coordinate of a point P3 by pointing to it with the cross shaped marker M by operating the mouse of the input unit 32, where the point P3 is located at the approximate middle of the long axis L1 in a region of the cardiac cavity $H_0$.

Figure 17:
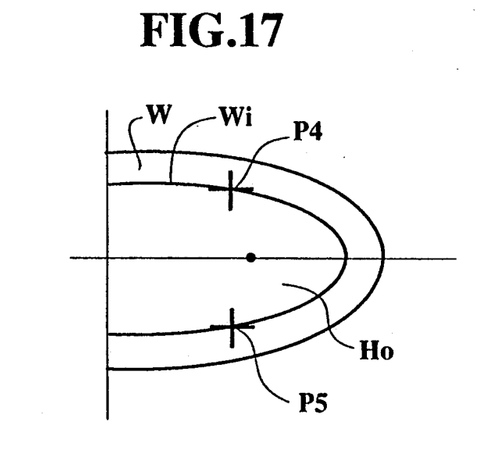

Then, as shown in FIG. 17, the operator specifies two arbitrary points P4 and P5 on the inner contour Wi of the cardiac muscle W by pointing to them with the cross shaped marker M by operating the mouse of the input unit 32.

Figure 18:
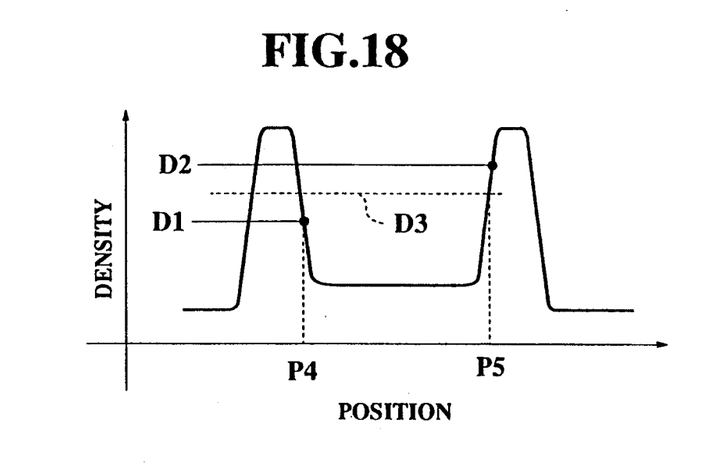
FIG. 18 is an illustration of a density profile data used in the procedure explained in FIGS. 15 to 17.

When these coordinates are specified, the threshold setting unit 37 reads density profile data shown in FIG. 18 from the image data in the display memory 36, and takes the higher one D2 of the densities for the points P4 and P5 as the upper threshold and the lower one D1 of the densities for the points P4 and P5 as the lower threshold.

Figure 19:
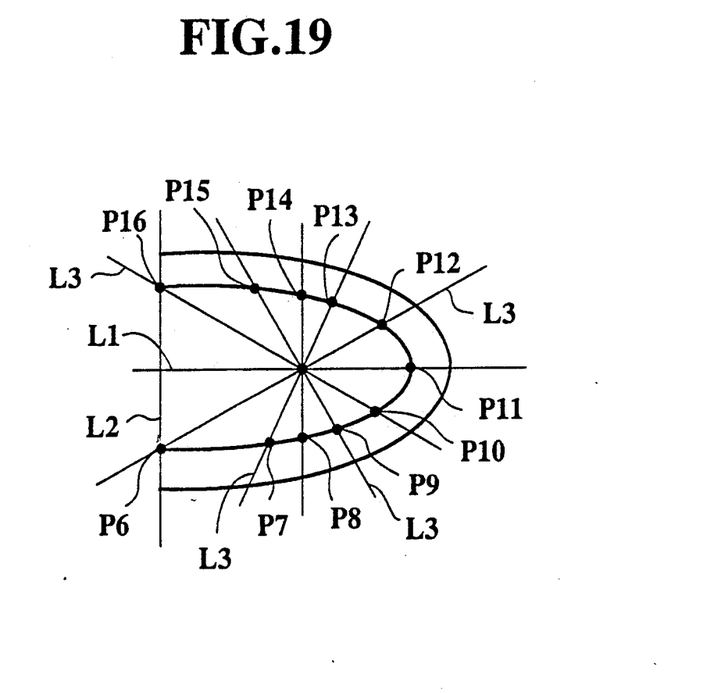
FIG. 19 is another illustration of a displayed tomographic image of a portion of a left ventricle for explaining the procedure explained in FIGS. 15 to 17.

Next, the boundary line generation unit 38 reads the data for the radial lines L3 from the graphic memory 34, and draws the radial lines L3 over the displayed image as shown in FIG. 19, where the radial lines L3 are lines intersecting at the point P3 at an angle of 30° with the neighboring ones. In addition, the boundary line generation unit 38 makes density profile data for the points on the radial lines L3 from the image data in the display memory 36, and determines the points P7 to P15 on the radial lines L3 which are the points on the cardiac cavity $H_0$ side of cardiac muscle W having the average value D3 shown in FIG. 18 of the upper threshold D2 and the lower threshold D1. Here, the operator inspects the automatically determined points P7 to P15 and corrects the incorrect points appropriately. For instance, in a case shown in FIG. 20 in which there is a high density blood tumor B inside the cardiac cavity $H_0$ near the cardiac muscle W, the point P9 may be located incorrectly on the blood tumor B when the boundary generation unit 38 determines the points. In such a case, the operator corrects the position of the point P9 to the position on the inner contour of the cardiac muscle W.

Next, the boundary line generation unit 38 draws the boundary line T starting from one intersection P6 of the inner contour Wi and the short axis L2 and toward another intersection P16 of the inner contour Wi and the short axis L2. Here, the boundary line T is determined by tracing the points having the half value D3 between the points P6 and P7 first, between the points P7 and P8 next, and so on, and by using a curve fitting for three neighboring points.

Figure 20:
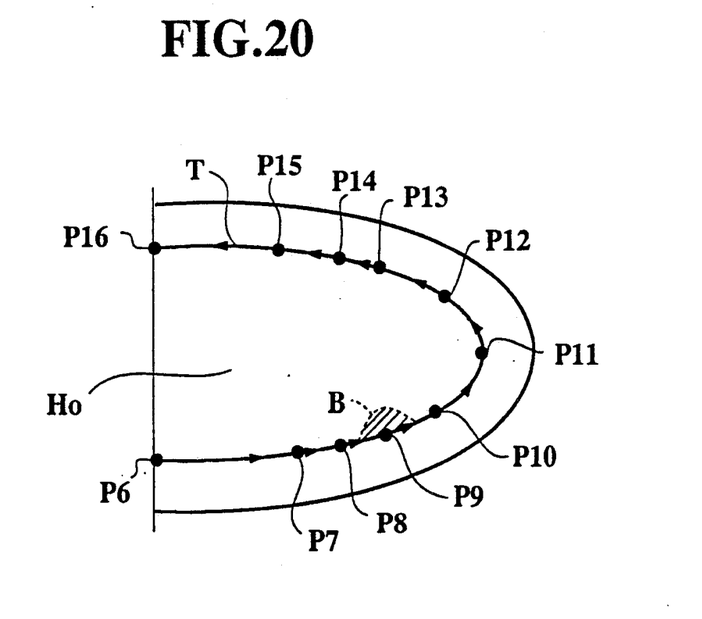
FIG. 20 is another illustration of a displayed tomographic image of a portion of a left ventricle for explaining an advantage of the procedure explained in FIGS. 15 to 19.

Thus, even in a case shown in FIG. 20 in which there is a high density blood tumor B inside the cardiac cavity $H_0$ near the cardiac muscle W, the boundary line is specified to pass through the point P9, so that the correct boundary line T as shown in FIG. 20 can be obtained.

When the boundary line T is completely drawn, the boundary line generation unit 38 applies the smoothing processing to the boundary line T to obtain the smooth contour.

Thus, according to this procedure, the contour can be obtained from the image efficiently and accurately.

It is to be noted that many modifications and variations of the above embodiments may be made without departing from the novel and advantageous features of the present invention. Accordingly, all such modifications and variations are intended to be included within the scope of the appended claims.

What is claimed is:

1. A method of evaluating a volume of a left ventricle of a heart, comprising the steps of:
   obtaining a right anterior oblique image and a 4-chamber image of the heart using nuclear magnetic resonance imaging, where the right anterior oblique image and the 4-chamber image are tomographic images for planes intersecting perpendicularly with each other at a straight line joining a mitral valve and a left ventricle apex;

determining contours of the left ventricle in the right anterior oblique image and the 4-chamber image obtained at the obtaining step;

measuring a prescribed number of sizes for the left ventricle from the contours determined at the determining step; and evaluating the volume of the left ventricle by using an orthogonal biplane Simpson's method and the sizes measured at the measuring step.

2. The method of claim 1, wherein at the obtaining step, the right anterior oblique image and the 4-chamber image are obtained by the steps of:

(A) carrying out a pilot scan imaging in a coronal plane in order to obtain a coronal tomographic image of the heart along the body axis;

(B) setting a first region of interest on the coronal tomographic image of the heart obtained at the step (A) along a straight line joining a lower side of an aortic valve and a left ventricle apex, and carrying out an imaging along the first region of interest in order to obtain a first intermediate tomographic image;

(C) setting a second region of interest on the first intermediate tomographic image obtained at the step (B) along a straight line passing through a widest region in a left atrium, and carrying out an imaging along the second region of interest in order to obtain a second intermediate tomographic image;

(D) setting a third region of interest on the second intermediate tomographic image obtained at the step (C) along an axis passing through the mitral valve and the left ventricle apex, and carrying out an imaging along the third region of interest in order to obtain a third intermediate tomographic image;

(E) setting a fourth region of interest on the third intermediate tomographic image obtained at the step (D) along a straight line perpendicular to the axis at an edge of the mitral valve, and carrying out an imaging along the fourth region of interest in order to obtain a fourth intermediate tomographic image;

(F) setting a fifth region of interest on the fourth intermediate tomographic image obtained at the step (E) along a straight line passing through a center of the left ventricle and a center of a interventricular septum, and carrying out an imaging along the fifth region of interest in order to obtain a fifth intermediate tomographic image;

(G) setting a sixth region of interest on the fifth intermediate tomographic image obtained at the step (F) along a straight line passing through the mitral valve and the left ventricle apex, and carrying out an imaging along the sixth region of interest in order to obtain the right anterior oblique image; and (H) setting a seventh region of interest on the right anterior oblique image obtained at the step (G) along a straight line passing through the mitral valve and the left ventricle apex, and carrying out an imaging along the seventh region of interest in order to obtain the 4-chamber image.

3. The method of claim 1, wherein at the determining step, the contours are determined by the steps of:

allowing an operator to specify two points on a contour portion in a displayed image;

determining upper and lower thresholds as densities at said two points specified by the operator; and tracing points having a particular density value between the upper and lower thresholds, to obtain the contour.

4. The method of claim 3, wherein at the tracing steps, a prescribed number of points having said particular density value are determined first, and the tracing is carried out between two neighboring points among said prescribed number of points successively.

5. The method of claim 1, wherein at the measuring step, the measured sizes are diameters of the contours at cross sections of a predetermined thickness.

6. The method of claim 5, wherein at the evaluating step, a shape of each cross section of the left ventricle is considered as an ellipse, a diameter of a contour determined from the right anterior oblique image at each said cross section is taken as a major axis of the ellipse, and a diameter of a contour determined from the 4-chamber image at each corresponding said cross section is taken as a minor axis of the ellipse.

* * * * *